(12) United States Patent
Unverricht et al.

(10) Patent No.: US 6,403,829 B1
(45) Date of Patent: Jun. 11, 2002

(54) METHOD FOR THE CATALYTIC GAS PHASE OXIDATION OF ACROLEIN INTO ACRYLIC ACID

(75) Inventors: Signe Unverricht; Heiko Arnold, both of Mannheim; Andreas Tenten, Maikammer; Ulrich Hammon, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/936,177

(22) PCT Filed: Feb. 28, 2000

(86) PCT No.: PCT/EP00/01633

§ 371 (c)(1),
(2), (4) Date: Sep. 10, 2001

(87) PCT Pub. No.: WO00/53559

PCT Pub. Date: Sep. 14, 2000

(30) Foreign Application Priority Data

Mar. 10, 1999 (DE) .......................... 199 10 508

(51) Int. Cl.⁷ .......................... C07C 51/16; C07C 51/10
(52) U.S. Cl. ...................... 562/532; 562/532; 562/531; 562/518

(58) Field of Search .................................. 562/532, 531, 562/518, 535

(56) References Cited

U.S. PATENT DOCUMENTS 5,264,625 A  *  11/1993  Hammon et al.
5,739,391 A  *   4/1998  Ruppel et al.

FOREIGN PATENT DOCUMENTS

| DE | 25 13 405 | 10/1976 |
| DE | 44 31 949 | 3/1995 |
| EP | 0 253 409 | 1/1988 |
| EP | 0 293 224 | 11/1988 |
| EP | 0 534 294 | 3/1993 |

* cited by examiner

*Primary Examiner*—Gary Geist
*Assistant Examiner*—Farhad Forohar
(74) *Attorney, Agent, or Firm*—Oblon, Spivak, McClelland, Maier & Neustadt, P.C.

(57) ABSTRACT

In a process for the catalytic gas-phase oxidation of acrolein to acrylic acid, the reaction gas starting mixture is passed, with an acrolein loading of $\geq 150$ l (s.t.p.)/l.h, over a fixed-bed catalyst which is housed in two spatially successive reaction zones A, B, the reaction zone B being kept at a higher temperature than the reaction zone A.

22 Claims, No Drawings

METHOD FOR THE CATALYTIC GAS PHASE OXIDATION OF ACROLEIN INTO ACRYLIC ACID

The present invention relates to a process for the catalytic gas-phase oxidation of acrolein to acrylic acid, in which a reaction gas starting mixture comprising acrolein, molecular oxygen and at least one inert gas, at least 20% by volume of which consists of molecular nitrogen, and containing the molecular oxygen and the acrolein in a molar ratio $O_2:C_3H_4O \geq 0.5$ is passed over a fixed-bed catalyst, whose active material is at least one molybdenum- and vanadium-containing multimetal oxide, in such a way that the acrolein conversion in a single pass is $\geq 90$ mol % and the associated selectivity of the acrylic acid formation is $\geq 90$ mol %.

The abovementioned process for the catalytic gas-phase oxidation of acrolein to acrylic acid is generally known (cf. for example EP-A 714700 or EP-A 700893 and the literature cited in these publications) and is important in particular as the second oxidation stage in the preparation of acrylic acid by two-stage catalytic gas-phase oxidation starting from propene. Acrylic acid is an important monomer which is used as such or in the form of an alkyl ester for producing polymers suitable, for example, as adhesives.

The object of any catalytic fixed-bed gas-phase oxidation of acrolein to acrylic acid is in principle to achieve a very high space-time yield (STY) with respect to desired product (in the case of a continuous procedure, this is the amount of acrylic acid in liters produced per hour and unit volume of the catalyst bed used).

There is therefore a general interest in carrying out the gas-phase oxidation with a very high loading of the catalyst bed with acrolein (this is understood as meaning the amount of acrolein in liters under standard temperature and pressure conditions (=l (s.t.p.); the volume in liters which the corresponding amount of acrolein would occupy under standard temperature and pressure conditions, i.e. at 25° C. and 1 bar) which is passed as a component of the reaction gas mixture per hour through one liter of catalyst bed), without significantly impairing the acrolein conversion occurring during a single pass of the reaction gas starting mixture through the catalyst bed and the selectivity of the associated formation of desired product.

The implementation of the abovementioned is adversely affected by the fact that the gas-phase oxidation of acrolein to acrylic acid on the one hand is highly exothermic and on the other hand is accompanied by a multiplicity of possible parallel and secondary reactions.

With increasing acrolein loading of the catalyst bed and implementation of the desired boundary condition of essentially constant acrolein conversion, it must therefore be assumed that, owing to the increased local heat production, the selectivity of the formation of desired product decreases.

The conventional processes for the catalytic gas-phase oxidation of acrolein to acrylic acid, wherein nitrogen is used as a main component of the inert diluent gas and in addition a fixed-bed catalyst present in a reaction zone and homogeneous along this reaction zone, i.e. of chemically uniform composition over the catalyst bed, is employed and the temperature of the reaction zone is kept at a value constant over the reaction zone (temperature of a reaction zone is understood here as meaning the temperature of the catalyst bed present in the reaction zone when the process is carried out in the absence of a chemical reaction; if this temperature is not constant within the reaction zone, the term temperature of a reaction zone means in this case the number average of the temperature of the catalyst bed along the reaction zone), therefore limit the value to be applied for the acrolein loading of the catalyst bed to values $\leq 150$ l (s.t.p.) of acrolein/l of catalyst bed.h (cf. for example EP-B 714700; there, the maximum acrolein loading used is 120 l (s.t.p.) of acrolein/l.h).

EP-B 253409 and the associated equivalent, EP-B 257565, disclose that, with the use of an inert diluent gas which has a higher molar heat capacity than molecular nitrogen, the proportion of propene in the reaction gas starting mixture of a two-stage gas-phase catalytic oxidation of propene to acrylic acid can be increased. Nevertheless, in the two abovementioned publications too, the maximum realized propene loading of the catalyst bed, and hence essentially automatically also an acrolein loading of the catalyst bed occurring subsequently on direct passage of the product gas mixture of the propene oxidation stage into the acrolein oxidation stage, are $\leq 140$ l (s.t.p.) of reactant (propene or acrolein)/l.h.

Only in EP-A 293224 have acrolein loadings above 150 l (s.t.p.) of acrolein/l.h been realized to date. However, this has been achieved at the expense of a special inert diluent gas to be used, which is completely free of molecular nitrogen. The particular disadvantage of this diluent gas is that, in contrast to molecular nitrogen, all its components are desired products which have to be at least partly recycled to the gas-phase oxidation in an expensive manner during a continuous process, for reasons of cost-efficiency.

It is an object of the present invention to provide a process, as defined at the outset, for the catalytic gas-phase oxidation of acrolein to acrylic acid, which ensures a high space-time yield of acrylic acid without having the disadvantages of the high-load procedure of the prior art.

We have found that this object is achieved by a process for the catalytic gas-phase oxidation of acrolein to acrylic acid, in which a reaction gas starting mixture comprising acrolein, molecular oxygen and at least one inert gas, at least 20% by volume of which consists of molecular nitrogen, and containing the molecular oxygen and the acrolein in a molar ratio $O_2:C_3H_4O \geq 0.5$ is passed, at elevated temperatures, over a fixed-bed catalyst, whose active material is at least one molybdenum- and vanadium-containing multimetal oxide, in such a way that the acrolein conversion in a single pass is $\geq 90$ mol % and the associated selectivity of the acrylic acid formation is $\geq 90$ mol %, wherein a) the loading of the fixed-bed catalyst where the acrolein contained in the reaction gas starting mixture is $\geq 150$ l (s.t.p.) of acrolein per l of catalyst bed per h, b) the fixed-bed catalyst consists of a catalyst bed arranged in two spatially successive reaction zones A, B, the temperature of the reaction zone A being from 230 to 270° C. and the temperature of the reaction zone B being from 250 to 300° C. and at the same time being at least 5° C. above the temperature of the reaction zone A, c) the reaction gas starting mixture flows first through the reaction zone A and then through the reaction zone B and d) the reaction zone A extends to an acrolein conversion of from 55 to 85 mol %.

Preferably, the reaction zone A extends to an acrolein conversion of from 65 to 80 mol %. In addition, the temperature of the reaction zone A is advantageously from 245 to 260° C. The temperature of the reaction zone B is preferably at least 10° C., particularly advantageously 20° C., above the temperature of the reaction zone A and is advantageously from 265 to 285° C.

The higher the chosen acrolein loading of the catalyst bed in the novel process, the greater should be the chosen difference between the temperature of the reaction zone A and the temperature of the reaction zone B. Usually, however, the abovementioned temperature difference in the novel process will be not more than 40° C., i.e. the difference between the temperature of the reaction zone A and the temperature of the reaction zone B can, according to the invention, be up to 15° C., up to 25° C., up to 30° C., up to 35° C. or up to 40° C.

Furthermore, in the novel process, the acrolein conversion based on the single pass may be $\geq 92$ mol % or $\geq 94$ mol % or $\geq 96$ mol % or $\geq 98$ mol % and frequently even $\geq 99$ mol %. The selectivity of the formation of desired product is as a rule $\geq 92$ mol % or $\geq 94$ mol %, frequently $\geq 95$ mol % or $\geq 96$ mol % or $\geq 97$ mol %, respectively.

Surprisingly, the abovementioned applies not only in the case of acrolein loadings of the catalyst bed of $\geq 150$ l (s.t.p.)/l.h or of $\geq 160$ l (s.t.p.)/l.h or $\geq 170$ l (s.t.p.)/l.h or $\geq 175$ l (s.t.p.)/l.h or $\geq 180$ l (s.t.p.)/l.h, but also in the case of acrolein loadings of the catalyst bed of $\geq 185$ l (s.t.p.)/l.h or of $\geq 190$ l (s.t.p.)/l.h or $\geq 200$ l (s.t.p.)/l.h or $\geq 210$ l (s.t.p.)/l.h and in the case of loadings of $\geq 220$ l (s.t.p.)/l.h or $\geq 230$ l (s.t.p.)/l.h or $\geq 240$ l (s.t.p.)/l.h or $\geq 250$ l (s.t.p.)/l.h.

It is surprising that the abovementioned values are achievable even when the inert gas used according to the invention comprises $\geq 30$% by volume or $\geq 40$% by volume or $\geq 50$% by volume or $\geq 60$% by volume or $\geq 70$% by volume or $\geq 80$% by volume or $\geq 90$% by volume or $\geq 95$% by volume of molecular nitrogen.

Expediently, the inert diluent gas in the novel process comprises from 5 to 20% by weight of $H_2O$ and from 70 to 90% by volume of $N_2$.

Apart from the components stated in this publication, the reaction gas starting mixture usually contains essentially no further components.

At acrolein loadings above 250 l (s.t.p.)/l.h, the presence of inert (inert diluent gases should in general be those which are converted to an extent of less than 5%, preferably less than 2%, in a single pass) diluent gases, such as propane, ethane, methane, butane, pentane, $CO_2$, CO, steam and/or noble gases, is recommended for the novel process. However, these gases can of course also be present in the case of lower loadings. It is also possible to use an inert gas consisting only of one or more of the abovementioned gases. It is also surprising that the novel process can be carried out using a catalyst bed which is homogeneous, i.e. chemically uniform, over both reaction zones, without suffering significant declines in conversion and/or in selectivity.

In the novel process, the acrolein loading usually does not exceed 600 l (s.t.p.)/l.h. Typically, the acrolein loadings in the novel process without significant loss of conversion and selectivity are $\leq 300$, frequently $\leq 250$, l (s.t.p.)/l.h.

The operating pressure in the novel process may be either below atmospheric pressure (for example down to 0.5 bar) or above atmospheric pressure. Typically, the operating pressure will be from 1 to 5, frequently from 1 to 3, bar. The reaction pressure usually will not exceed 100 bar.

According to the invention, the molar ratio of $O_2$:acrolein in the reaction gas starting mixture must be $\geq 0.5$. Often it is $\geq 1$. Usually, this ratio is $\leq 3$. According to the invention, the molar ratio of $O_2$:acrolein in the reaction gas starting mixture is frequently from 1 to 2 or from 1 to 1.5.

A suitable source of the molecular oxygen required in the novel process is air, as well as air depleted in molecular nitrogen (e.g. $\geq 90$% by volume of $O_2$, $\leq 10$% by volume of $N_2$).

According to the invention, the amount of acrolein in the reaction gas starting mixture may be, for example, from 3 to 15, frequently from 4 to 10% by volume or from 5 to 8% by volume (based in each case on the total volume).

Frequently, the novel process is carried out at an acrolein:oxygen:steam:inert gas volume ratio (l (s.t.p.)) of 1:(0.5 or 1 to 3):(0 to 20):(3 to 30), preferably of 1:(1 to 3):(0.5 to 10):(7 to 8).

Acrolein produced by catalytic gas-phase oxidation of propene is usually used in the novel process. As a rule, the acrolein-containing reaction gases of this propene oxidation are used without intermediate purification, and it is for this reason that the novel reaction gas starting mixture can also contain small amounts of, for example, unconverted propene or of byproducts of the propene oxidation. The oxygen required for the acrolein oxidation must usually also be added to the product gas mixture of the propene oxidation.

Such a catalytic gas-phase oxidation of propene to acrolein prior to the novel process is advantageously carried out, analogously to the novel process, so that a reaction gas starting mixture comprising propene, molecular oxygen and at least one inert gas, at least 20% by volume of which consists of molecular nitrogen, and containing the molecular oxygen and the propene in a molar ratio $O_2$:$C_3H_6$ of $\geq 1$ is passed, at elevated temperatures, over a fixed-bed catalyst whose active material is at least one molybdenum- and/or tungsten- and bismuth-, tellurium-, antimony-, tin- and/or copper-containing multimetal oxide, in such a way that the propene conversion during a single pass is $\geq 90$ mol % and the associated selectivity of the acrolein formation and of the acrylic acid byproduct formation together is $\geq 90$ mol %, in which oxidation a) the loading of the fixed-bed catalyst with the propene contained in the reaction gas starting mixture is $\geq 160$ l (s.t.p.) of propene per l of catalyst bed per h, b) the fixed-bed catalyst consists of a catalyst bed arranged in two spatially successive reaction zones A', B', the temperature of the reaction zone A' being from 300 to 330° C. and the temperature of the reaction zone B being from 300 to 365° C. and at the same time being at least 5° C. above the temperature of the reaction zone A', c) the reaction gas starting mixture flows first through the reaction zone A' and then through the reaction zone B' and d) the reaction zone A' extends to a propene conversion of from 40 to 80 mol %.

Particularly suitable catalysts for the abovementioned gas-phase catalytic propene oxidation are those of EP-A 15565, EP-A 575897, DE-A 19746210 and DE-A 19855913.

Suitable fixed-bed catalysts for the novel gas-phase catalytic acrolein oxidation are all those whose active material is at least one Mo- and V-containing multimetal oxide. Such suitable multimetal oxide catalysts are disclosed, for example, in U.S. Pat. Nos. 3,775,474, 3,954,855, 3,893,951 and 4,339,355. Also particularly suitable are the multimetal oxide materials of EP-A 427508, DE-A 2909671, DE-A 3151805, DE-B 2626887, DE-A 4302991, EP-A 700893, EP-A 714700 and DE-A 19736105.

Particularly preferred in this context are the exemplary embodiments of EP-A 714700 and DE-A 19736105.

A multiplicity of the multimetal oxide active materials suitable according to the invention can be described by the formula I $$Mo_{12}V_aX^1{}_bX^2{}_cX^3{}_dX^4{}_eX^5{}_fX^6{}_gO_n \qquad (I),$$

where $X^1$ is W, Nb, Ta, Cr and/or Ce, $X^2$ is Cu, Ni, Co, Fe, Mn and/or Zn, $X^3$ is Sb and/or Bi, $X^4$ is one or more alkali metals, $X^5$ is one or more alkaline earth metals, $X^6$ is Si, Al, Ti and/or Zr, a is from 1 to 6, b is from 0.2 to 4, c is from 0.5 to 18, d is from 0 to 40, e is from 0 to 2, f is from 0 to 4, g is from 0 to 40 and n is a number which is determined by the valency and frequency of the elements in I other than oxygen.

Preferred embodiments among the active multimetal oxides I are those which are covered by the following meanings of the variables of the formula I:

$X^1$ is W, Nb and/or Cr, $X^2$ is Cu, Ni, Co and/or Fe, $X^3$ is Sb, $X^4$ is Na and/or K, $X^5$ is Ca, Sr and/or Ba, $X^6$ is Si, Al and/or Ti, a is from 2.5 to 5, b is from 0.5 to 2, c is from 0.5 to 3, d is from 0 to 2, e is from 0 to 0.2, f is from 0 to 1 and n is a number which is determined by the valency and frequency of the elements I other than oxygen.

Very particularly preferred multimetal oxides I are, however, those of the formula I'

$$Mo_{12}V_{a'}Y^1_{b'}Y^2_{c'}Y^5_{f'}Y^6_{g'}O_{n'} \quad (I')$$

where $Y^1$ is W and/or Nb, $Y^2$ is Cu and/or Ni, $Y^5$ is Ca and/or Sr, $Y^6$ is Si and/or Al, a' is from 2 to 4, b' is from 1 to 1.5, c' is from 1 to 3, f' is from 0 to 0.5, g' is from 0 to 8 and n' is a number which is determined by the valency and frequency of the elements in I' other than oxygen.

The multimetal oxide active materials (I) suitable according to the invention are obtainable in a known manner and disclosed, for example, in DE-A 4335973 or in EP-A 714700.

In principle, multimetal oxide active materials suitable according to the invention, in particular those of the formula I, can be prepared in a simple manner by producing, from suitable sources of the elemental constituents, a very intimate, preferably finely divided dry blend having a composition corresponding to their stoichiometry and calcining said dry blend at from 350 to 600° C. The calcination can be carried out either under inert gas or under an oxidizing atmosphere, e.g. air (mixture of inert gas and oxygen) or under a reducing atmosphere (for example mixtures of inert gas and reducing gases, such as $H_2$, NH3, CO, methane and/or acrolein or said reducing gases by themselves). The duration of calcination may be from a few minutes to a few hours and usually decreases with the temperature. Suitable sources of the elemental constituents of the multimetal oxide active materials I are those compounds which are already oxides and/or those compounds which can be converted into oxides by heating, at least in the presence of oxygen.

The intimate mixing of the starting compounds for the preparation of multimetal oxide materials I can be carried out in dry or in wet form. If it is carried out in dry form, the starting compounds are expediently used in the form of finely divided powder and, after mixing and any compaction, are subjected to calcination. However, the intimate mixing is preferably carried out in wet form.

Usually, the starting compounds are mixed with one another in the form of an aqueous solution and/or suspension. Particularly intimate dry blends are obtained in the mixing process described when exclusively dissolved sources of the elemental constituents are used as starting materials. A preferably used solvent is water. The aqueous material obtained is then dried, the drying process preferably being carried out by spray-drying the aqueous mixture at outlet temperatures of from 100 to 150° C.

The multimetal oxide materials suitable according to the invention, in particular those of the formula I, can be used for the novel process both in powder form and after shaping to specific catalyst geometries, where the shaping may be effected before or after the final calcination. For example, unsupported catalysts can be prepared from the powder form for the active material or its uncalcined precursor material by compaction to give the desired catalyst geometry (for example by pelleting, or extrusion), it being possible, if required, to add assistants, such as graphite or stearic acid as lubricants and/or molding assistants and reinforcing agents, such as microfibers of glass, asbestos, silicon carbide or potassium titanate. Suitable geometries of unsupported catalysts are, for example, solid cylinders or hollow cylinders having an external diameter and a length of from 2 to 10 mm. In the case of the hollow cylinders, a wall thickness of from 1 to 3 mm is expedient. The unsupported catalyst can of course also have spherical geometry, it being possible for the sphere diameter to be from 2 to 10 mm.

The pulverulent active material or its pulverulent, still uncalcined precursor material can of course also be shaped by application to premolded inert catalyst carriers. The coating of the carriers for the preparation of the coated catalysts is carried out, as a rule, in a suitable rotatable container, as disclosed, for example, in DE-A 2909671, EP-A 293859 or EP-A 714700.

Expediently, for coating the carriers, the powder material to be applied is moistened and, after the application, is dried again, for example by means of hot air. The layer thickness of the powder material applied to the carrier is expediently chosen to be from 10 to 1000 $\mu$m, preferably from 50 to 500 $\mu$m, particularly preferably from 150 to 250 $\mu$m.

Conventional porous or nonporous aluminas, silica, thorium dioxide, zirconium dioxide, silicon carbide or silicates, such as magnesium silicate or aluminum silicate, can be used as carrier materials. The carriers may have a regular or irregular shape, those having a regular shape and substantial surface roughness, for example spheres or hollow cylinders, being preferred. The use of essentially nonporous, spherical steatite carriers which have a rough surface and whose diameter is from 1 to 8 mm, preferably from 4 to 5 mm, is preferred. However, the use of cylinders whose length is from 2 to 10 mm and whose external diameter is from 4 to 10 mm as carriers is also suitable. Where rings suitable according to the invention are used as carriers, the wall thickness is moreover usually from 1 to 4 mm. Annular carriers preferably to be used according to the invention have a length of from 3 to 6 mm, an external diameter of from 4 to 8 mm and a wall thickness of from 1 to 2 mm. Rings measuring 7 mm x 3 mm x 4 mm (external diameter x length x internal diameter) are also particularly suitable according to the invention as carriers. The fineness of the catalytically active oxide materials to be applied to the surface of the carrier is of course adapted to the desired coat thickness (cf. EP-A 714700).

Advantageous multimetal oxide active materials to be used according to the invention are furthermore materials of the formula II, $$[D]_p[E]_q \qquad (II),$$

where:

D is $Mo_{12}V_{a''}Z^1_{b''}Z^2_{c''}Z^3_{d''}Z^4_{e''}Z^5_{f''}Z^6_{g''}O_{x''}$,

E is $Z^7_{12}Cu_{h''}H_{i''}O_{y''}$, $Z^1$ is W, Nb, Ta, Cr and/or Ce, $Z^2$ is Cu, Ni, Co, Fe, Mn and/or Zn, $Z^3$ is Sb and/or Bi, $Z^4$ is Li, Na, K, Rb, Cs and/or H, $Z^5$ is Mg, Ca, Sr and/or Ba, $Z^6$ is Si, Al, Ti and/or Zr, $Z^7$ is Mo, W, V, Nb and/or Ta, a" is from 1 to 8, b" is from 0.2 to 5, c" is from 0 to 23, d" is from 0 to 50, e" is from 0 to 2, f" is from 0 to 5, g" is from 0 to 50, h" is from 4 to 30, i" is from 0 to 20 and x",y" are numbers which are determined by the valency and frequency of the elements in II other than oxygen and p,q are numbers other than zero, whose ratio p/q is from 160:1 to 1:1, which are obtainable by separately preforming a multimetal oxide material E $$Z^7_{12}Cu_{h''}H_{i''}O_{y''} \qquad (E),$$

in finely divided form (starting material 1) and then incorporating the preformed solid starting material 1 into an aqueous solution, an aqueous suspension or a finely divided dry blend of sources of the elements Mo, V, $Z^1$, $Z^2$, $Z^3$, $Z^4$, $Z^5$ and $Z^6$, which contains the abovementioned elements in the stoichiometry D $$Mo_{12}V_{a''}Z^1_{b''}Z^2_{c''}Z^3_{d''}Z^4_{e''}Z^5_{f''}Z^6_{g''} \qquad (D),$$

(starting material 2), in the desired ratio p:q, drying any resulting aqueous mixture and calcining the resulting dry precursor material before or after its drying to the desired catalyst geometry at from 250 to 600° C.

Preferred multimetal oxide materials II are those in which the incorporation of the preformed solid starting material 1 into an aqueous starting material 2 is effected at ≦70° C. A detailed description of the preparation of catalysts comprising multimetal oxide materials II is contained, for example, in EP-A 668104, DE-A 19736105 and DE-A 19528646.

Regarding the shaping of catalysts comprising multimetal oxide materials II, the statements made in connection with the catalysts comprising multimetal oxide materials I are applicable.

The novel process is carried out in a technically expedient manner in a two-zone tube-bundle reactor. A preferred variant of a two-zone tube-bundle reactor which may be used according to the invention is disclosed in DE-C 2830765. However, the two-zone tube-bundle reactors disclosed in DE-C 2513405, U.S. Pat. No. 3,147,084, DE-A 2201528 and DE-A 2903582 are also suitable for carrying out the novel process.

This means that, in a simple procedure, the fixed-bed catalyst to be used according to the invention is present in the metal tubes of a tube-bundle reactor, and two heating media, as a rule salt melts, essentially spatially separate from one another are passed around the metal tubes. The tube section over which the respective salt bath extends represents, according to the invention, a reaction zone.

This means that, in a simple procedure, a salt bath A flows around those sections of the tubes (the reaction zone A), in which the oxidative conversion of the acrolein (in a single pass) takes place until a conversion of from 55 to 85 mol % is reached and a salt bath B flows around that section of the tubes (the reaction zone B) in which the subsequent oxidative conversion of the acrolein (in a single pass) takes place until a conversion of at least 90 mol % is achieved (if required, further reaction zones which are kept at individual temperature may follow the reaction zones A, B to be used according to the invention).

It is technically expedient if the novel process comprises no further reaction zones, i.e. the salt bath B expediently flows around that section of the tubes in which the subsequent oxidative conversion of the acrolein (in a single pass) takes place to a conversion of ≧92 mol % or ≧94 mol % or ≧96 mol % or ≧98 mol % and frequently even ≧99 mol % or more.

Usually, the beginning of the reaction zone B is behind the maximum hot spot of the reaction zone A. The temperature of the maximum hot spot of the reaction zone B is usually below the temperature of the maximum hot spot of the reaction zone A.

According to the invention, the two salt baths A, B can be passed cocurrent or countercurrent through the space surrounding the reaction tubes, relative to the direction of flow of the reaction mixture flowing through the reaction tubes. According to the invention, it is of course also possible to use cocurrent flow in the reaction zone A and countercurrent flow in the reaction zone B (or vice versa).

In all the abovementioned configurations within the respective reaction zone, it is of course possible also to superpose a transverse flow on the flow of the salt melt which is parallel to the reaction tubes, so that the individual reaction zone corresponds to a tube-bundle reactor as described in EP-A 700714 or in EP-A 700893, and overall a meandering flow of the heat exchange medium results in the longitudinal section through the catalyst tube bundle.

Expediently, the reaction gas starting mixture is preheated to the reaction temperature before being fed to the catalyst bed.

In the abovementioned tube-bundle reactors, the catalyst tubes are usually made of ferritic steel and typically have a wall thickness of from 1 to 3 mm. Their internal diameter is as a rule from 20 to 30 mm, frequently from 22 to 26 mm. It is technically expedient if the number of catalyst tubes housed in the tube bundle container is at least 5000, preferably at least 10,000. Frequently, the number of catalyst tubes housed in the reaction container is from 15,000 to 30,000. Tube-bundle reactors having more than 40,000 catalyst tubes tend to be the exception. Inside the container, the catalyst tubes are usually homogeneously distributed, the distribution expediently being chosen so that the distance between the central inner axes of catalyst tubes closest to one another (the catalyst tube spacing) is from 35 to 45 mm (cf. EP-B 468290).

Particularly suitable heat exchange media are fluid heating media. The use of melts of salts such as potassium nitrate, potassium nitrite, sodium nitrite and/or sodium nitrate, or of metals having a low melting point, such as sodium, mercury or alloys of various metals, is particularly advantageous.

In all the abovementioned configurations of the flow in the two-zone tube-bundle reactors, the flow rate inside the two required circulations of heat exchange media is as a rule chosen so that the temperature of the heat exchange medium increases by from 0 to 15° C. from the entry into the reaction zone to the exit out of the reaction zone, i.e., according to the invention, the abovementioned $\Delta T$ may be from 1 to 10° C. or from 2 to 8° C. or from 3 to 6° C.

The temperature at which the heat exchange medium enters the reaction zone A is, according to the invention, usually from 230 to 270° C. The temperature at which the heat exchange medium enters the reaction zone B is, according to the invention, on the one hand usually from 250° C. to 300° C. and on the other hand is simultaneously at least 5° C. above the temperature of the heat exchange medium entering the reaction zone A.

Preferably, the temperature at which the heat exchange medium enters the reaction zone B is at least 10° C. or at least 20° C. above the temperature of the heat exchange medium entering the reaction zone A. According to the invention, the difference between the temperatures at entry into the reaction zones A and B may thus be up to 15° C., up to 25° C., up to 30° C., up to 35° C. or up to 40° C. However, the abovementioned temperature is usually not more than 50° C. The higher the chosen acrolein loading of the catalyst bed in the novel process, the greater should be the difference between the temperature at which the heat exchange medium enters the reaction zone A and the temperature at which the heat exchange medium enters the reaction zone B. Preferably, the temperature at entry into the reaction zone A is from 245 to 260° C. and the temperature at entry into the reaction zone B is from 265 to 285° C.

In the novel process, the two reaction zones A, B can of course also be realized in tube-bundle reactors spatially separated from one another. If required, a heat exchanger may also be mounted between the two reaction zones A, B. The two reaction zones A, B can of course also be designed as a fluidized bed.

Furthermore, in the novel process, it is also possible to use a catalyst bed whose volume-specific activity in the direction of flow of the reaction gas mixture increases continuously, abruptly or stepwise (this can be achieved, for example, by dilution with inert material or variation of the activity of the multimetal oxide).

For the two-zone procedure described, it is also possible to use the inert diluent gases recommended in EP-A 293224 and in EP-B 257565 (for example, only propane or only methane, etc.). The latter can, if required, also be combined with a volume-specific catalyst bed activity which decreases in the direction of flow of the reaction gas mixture.

It should once again be pointed out here that, for carrying out the novel process, it is also possible to use in particular the two-zone tube-bundle reactor type which is described in DE-B 40 2201528 and which includes the possibility of diverting a portion of the relatively hot heat exchange medium of the reaction zone B to the reaction zone A in order, if required, to heat up a cold reaction gas starting mixture or a cold recycled gas.

The novel process is particularly suitable for a continuous procedure. It is surprising that it permits a high space-time yield in the formation of the desired product in a single pass without simultaneously significantly impairing the selectivity of formation of the desired product. Rather, there is generally an increase in the selectivity of formation of the desired product. The latter is presumably due to the fact that, owing to the higher temperatures present in the region of the higher acrolein conversion, the novel process results in less readsorption of the resulting acrylic acid onto the fixed-bed catalyst.

Also noteworthy is the fact that the catalyst life in the novel process is completely satisfactory in spite of the extreme catalyst loading with reactants.

In the novel process, pure acrylic acid is not obtained, but instead a mixture from whose secondary components the acrylic acid can be separated off in a manner known per se (for example by rectification and/or crystallization). Unconverted acrolein, propene and inert diluent gas used and/or formed in the course of the reaction can be recycled to the gas-phase oxidation. In a two-stage gas-phase oxidation starting from propene, the recycling is expediently effected into the first oxidation stage. The novel two-zone procedure can of course, if required, also be used in the case of conventional propene loads.

Furthermore, unless mentioned otherwise, conversion, selectivity and residence time are defined as follows in this publication:

$$\text{Conversion } C_A \text{ of acrolein (\%)} = \frac{\text{Number of moles of acrolein converted}}{\text{Number of moles of acrolein used}} \times 100$$

$$\text{Selectivity } S_A \text{ of the acrylic acid formation (\%)} = \frac{\text{Number of moles of acrolein converted to acrylic acid}}{\text{Number of moles of acrolein converted}} \times 100$$

$$\text{Residence time (sec)} = \frac{\text{Empty reactor volume filled with catalyst (l)}}{\text{Throughput of reaction gas starting mixture (l/h)}} \times 3600$$

EXAMPLES a) Catalyst Preparation

1. Preparation of the Catalytically Active Oxide Material $Mo_{12}V_3W_{1.2}Cu_{2.4}O_n$ 190 g of copper(II) acetate monohydrate were dissolved in 2700 g of water to give a solution I. 860 g of ammonium heptamolybdate tetrahydrate, 143 g of ammonium metavanadate and 126 g of ammonium paratungstate heptahydrate were dissolved in succession in 5500 g of water at 95° C. to give a solution II. The solution I was then stirred all at once into the solution II, after which a 25% strength by weight aqueous $NH_3$ solution was added in an amount sufficient to form a solution again. This was spray-dried at an outlet temperature of 110° C. The resulting spray-dried powder was kneaded with 0.25 kg, per kg of powder, of a 30% strength by weight aqueous acetic acid solution using a ZS1-80 type kneader from Werner & Pfleiderer and then dried at 110° C. for 10 hours in a drying oven.

700 g of the catalyst precursor thus obtained were calcined in an air/nitrogen mixture [(200 l of $N_2$/15 l of air)/h] in a rotary tubular furnace (50 cm long, 12 cm internal diameter).

During the calcination, the kneaded material was first continuously heated from room temperature (about 25° C.) to 325° C. in the course of one hour. The temperature was then maintained for 4 hours. Thereafter, heating was effected to 400° C. in the course of 15 minutes, this temperature was maintained for 1 hour and this was followed by cooling to room temperature.

The calcined catalytically active material was milled to give a finely divided powder, 50% of the powder particles of which passed through a sieve of mesh size from 1 to 10 μm and whose particle fraction having a maximum dimension above 50 μm was less than 1%.

b) Preparation of a Coated Catalyst 28 kg of annular carriers (7 mm external diameter, 3 mm length, 4 mm internal diameter, steatite, having a surface roughness Rz according to EP-B 714700 of 45 μm and a total pore volume, based on the volume of the carriers, of ≦1% by volume, manufacturer: Caramtec DE) were introduced into a 200 l coating pan (angle of inclination 90°; Hicoater from Lödige, DE). The coating pan was then rotated at 16 rpm. 2000 g of an aqueous solution consisting of 75% by weight of $H_2O$ and 25% by weight of glycerol were sprayed via a nozzle onto the carriers in the course of 25 minutes. At the same time, 7 kg of the catalytically active oxide powder from a) were simultaneously metered in continuously in the same period via a vibratory conveyor outside the spray cone of the atomizer nozzle. During the coating, the powder fed in was completely absorbed onto the surface of the carriers and no agglomeration of the finely divided active oxide material was observed. After the end of the addition of powder and aqueous solution, hot air at 110° C. was blown into the coating pan for 20 minutes at a speed of 2 rpm. Drying was then carried out for a further 2 hours at 250° C. in the stationary bed (tray oven) under air. Annular coated catalysts whose content of active oxide material was 20% by weight, based on the total mass, were obtained. The coat thickness was 230±25 μm both over the surface of a carrier and over the surface of different carriers.

b) Gas-phase Catalytic Oxidation of Acrolein to Acrylic Acid

1. Loading the Reaction Tube

A V2A steel reaction tube having an external diameter of 30 mm, a wall thickness of 2 mm, an internal diameter of 26 mm and a length of 439 cm and having a thermocouple tube (4 mm external diameter) centered in the middle of the reaction tube for receiving a thermocouple with which the temperature in the reaction tube can be determined was loaded from the bottom upward on a catalyst support ledge (44 cm length) first with steatite beads having a rough surface (from 4 to 5 mm diameter, inert material for heating the reaction gas starting mixture) over a length of 30 cm and then with the coated catalyst rings prepared in a) over a length of 300 cm, before the loading was completed with the abovementioned steatite beads as a subsequent bed over a length of 30 cm. The remaining 35 cm of catalyst tube were left empty.

That part of the reaction tube which was loaded with solid was thermostatted by means of 12 aluminum blocks cast cylindrically around the tube and each having a length of 30 cm (comparative experiments using a corresponding reaction tube heated by means of a salt bath through which nitrogen was bubbled showed that thermostatting by means of an aluminum block was capable of simulating thermostatting by means of a salt bath). The first six aluminum blocks in the direction of flow defined a reaction zone A and the remaining six aluminum blocks defined a reaction zone B. The ends of the reaction tube which were free of solid were kept at 220° C. by means of steam under pressure.

The reaction tube described above was loaded continuously with a reaction gas starting mixture of the following composition, the loading and the thermostatting of the reaction tube being varied:

5.5% by volume of acrolein, 0.3% by volume of propene, 6.0% by volume of molecular oxygen, 0.4% by volume of CO, 0.8% by volume of $CO_2$, 9.0% by volume of water and 78.0% by volume of molecular nitrogen.

A small sample was taken from the product gas mixture at the reaction tube outlet for gas chromatographic analysis. An analysis point was likewise present at the end of the reaction zone A.

The results obtained as a function of the chosen acrolein loading and of the chosen aluminum thermostatting are shown in Table 1 below.

$T_A$ is the temperature of the aluminum blocks in the reaction zone A and $T_B$ is the temperature of the aluminum blocks in the reaction zone B.

$C_{AA}$ is the acrolein conversion at the end of the reaction zone A and $C_{AE}$ is the acrolein conversion at the reaction tube outlet. $S_{AE}$ is the selectivity of the acrylic acid formation at the reaction tube outlet and $STY_A$ is the space-time yield of acrylic acid at the reaction tube outlet.

Finally, it may be stated, that, instead of the catalyst bed used in the example, a corresponding bed according to Example 3 of DE-A 19736105 may also be used.

TABLE 1

| Acrolein loading [l (s.t.p.) of acrolein/l · h] | $T_A$ [° C.] | $T_B$ [° C.] | $C_{AA}$ (%) | $C_{AE}$ (%) | $S_{AE}$ (%) | $STY_A$ (g/l · h) |
|---|---|---|---|---|---|---|
| 87 | 255 | 255 | 91.5 | 99.2 | 95.7 | 265 |
| 113 | 262 | 262 | 91.7 | 99.3 | 95.3 | 345 |
| 150 | 267 | 267 | 93.2 | 99.3 | 95.0 | 452 |
| 150 | 254 | 271 | 76.1 | 99.3 | 95.8 | 457 |
| 171 | 255 | 276 | 73.2 | 99.3 | 95.7 | 523 |

If the acrolein load is increased to >175 l (s.t.p.) of acrolein/l.h, the results according to Table 2 are obtained.

TABLE 2

| Acrolein loading [l (s.t.p.) of acrolein/l · h] | $T_A$ [° C.] | $T_B$ [° C.] | $C_{AA}$ (%) | $C_{AE}$ (%) | $S_{AE}$ (%) | $STY_A$ (g/l · h) |
|---|---|---|---|---|---|---|
| 190 | 257 | 281 | 78.2 | 99.3 | 95.7 | 579 |
| 210 | 257 | 286 | 71.7 | 99.3 | 95.6 | 640 |

We claim:

1. A process for the catalytic gas-phase oxidation of acrolein to acrylic acid, in which a reaction gas starting mixture comprising acrolein, molecular oxygen and at least one inert gas, at least 20% by volume of which consists of molecular nitrogen, and containing the molecular oxygen and the acrolein in a molar ratio $O_2:C_3H_4O \geq 0.5$ is passed, at elevated temperatures, over a fixed-bed catalyst, whose active material is at least one molybdenum- and vanadium-containing multimetal oxide, in such a way that the acrolein conversion in a single pass is $\geq 90$ mol % and the associated selectivity of the acrylic acid formation is $\geq 90$ mol %, wherein
   a) the loading of the fixed-bed catalyst where the acrolein contained in the reaction gas starting mixture is $\geq 150$ l (s.t.p.) of acrolein per l of catalyst bed per h,
   b) the fixed-bed catalyst consists of a catalyst bed arranged in two spatially successive reaction zones A, B, the temperature of the reaction zone A being from 230 to 270° C. and the temperature of the reaction zone B being from 250 to 300° C. and at the same time being at least 5° C. above the temperature of the reaction zone A,
   c) the reaction gas starting mixture flows first through the reaction zone A and then through the reaction zone B and
   d) the reaction zone A extends to an acrolein conversion of from 55 to 85 mol %.

2. A process as claimed in claim 1, wherein the reaction zone A extends to an acrolein conversion of from 65 to 80 mol %.

3. A process as claimed in claim 1, wherein the temperature of the reaction zone B is at least 20° C. above that of the reaction zone A.

4. A process as claimed in claim 1, wherein the temperature of the reaction zone A is from 245 to 260° C.

5. A process as claimed in claim 1, wherein the temperature of the reaction zone B is from 265 to 285° C.

6. A process as claimed in claim 1, wherein the acrolein conversion in a single pass is $\geq 94$ mol %.

7. A process as claimed in claim 1, wherein the selectivity of the acrylic acid formation is $\geq 94$ mol %.

8. A process as claimed in claim 1, wherein the acrolein loading of the catalyst bed is $\geq 160$ l (s.t.p.)/l.h.

9. A process as claimed in claim 1, wherein the acrolein loading of the catalyst bed is $\geq 170$ l (s.t.p.)/l.h.

10. A process as claimed in claim 1, wherein the one or more inert gases comprise $\geq 40\%$ by volume of molecular nitrogen.

11. A process as claimed in claim 1, wherein the one or more inert gases comprise steam.

12. A process as claimed in claim 1, wherein the one or more inert gases comprise $CO_2$ and/or CO.

13. A process as claimed in claim 1, which is carried out at an operating pressure of from 0.5 to 3 bar.

14. A process as claimed in claim 1, wherein the molar $O_2$:acrolein ratio in the reaction gas starting mixture is from 1 to 2.

15. A process as claimed in claim 1, wherein air is concomitantly used as an oxygen source.

16. A process as claimed in claim 1, wherein the acrolein content of the reaction gas starting mixture is from 3 to 15% by volume.

17. A process as claimed in claim 1, wherein the acrolein content of the reaction gas starting mixture is from 5 to 8% by volume.

18. A process as claimed in claim 1, wherein the active material of the fixed-bed catalyst is at least one multimetal oxide of the formula I $$Mo_{12}V_aX^1_bX^2_cX^3_dX^4_eX^5_fX^6_gO_n \qquad (I)$$

where
   $X^1$ is W, Nb, Ta, Cr and/or Ce,
   $X^2$ is Cu, Ni, Co, Fe, Mn and/or Zn,
   $X^3$ is Sb and/or Bi,
   $X^4$ is one or more alkali metals,
   $X^5$ is one or more alkaline earth metals,
   $X^6$ is Si, Al, Ti and/or Zr,
   a is from 1 to 6,
   b is from 0.2 to 4,
   c is from 0.5 to 18,
   d is from 0 to 40,
   e is from 0 to 2,
   f is from 0 to 4,
   g is from 0 to 40 and
   n is a number which is determined by the valency and frequency of the elements in I other than oxygen.

19. A process as claimed in claim 1, wherein the active material of the fixed-bed catalyst is at least one multimetal oxide of the formula II $$[D]_p[E]_q \qquad (II),$$

where
   D is $Mo_{12}V_{a''}Z^1_{b''}Z^2_{c''}Z^3_{d''}Z^4_{e''}Z^5_{f''}Z^6_{g''}O_{x''}$,
   E is $Z^7_{12}Cu_{h''}H_{i''}O_{y''}$,

$Z^1$ is W, Nb, Ta, Cr, and/or Ce,
   $Z^2$ is Cu, Ni, Co, Fe, Mn and/or Zn,
   $Z^3$ is Sb and/or Bi,
   $Z^4$ is Li, Na, K, Rb, Cs and/or H
   $Z^5$ is Mg, Co, Sr and/or Ba,
   $Z^6$ is Si, Al, Ti and/or Zr,
   $Z^7$ is Mo, W, V, Nb and/or Ta,
   a" is from 1 to 8,
   b" is from 0.2 to 5,
   c" is from 0 to 23,
   d" is from 0 to 50,
   e" is from 0 to 2,
   f" is from 0 to 5,
   g" is from 0 to 50, h" is from 4 to 30, i" is from 0 to 20 and x", y" are numbers which are determined by the valency and frequency of the elements in II other than oxygen and p, q are numbers other than zero, whose ratio p/q is from 160:1 to 1:1, which is obtainable by separately preforming a multimetal oxide material (E)

$$Z^7{}_{12}Cu_{h''}H_{i''}O_{y''} \qquad (E),$$

in finely divided form (starting material 1) and then incorporating the preformed solid starting material 1 into an aqueous solution, an aqueous suspension or a finely divided dry blend of sources of the elements Mo, V, $Z^1$, $Z^2$, $Z^3$, $Z^4$, $Z^5$ and $Z^6$, which contains the abovementioned elements in the stoichiometry D $$Mo_{12}V_{a''}Z^1{}_{b''}Z^2{}_{c''}Z^3{}_{d''}Z^4{}_{e''}Z^5{}_{f''}Z^6{}_{g''} \qquad (D)$$

(starting material 2), in the desired ratio p:q, drying any resulting aqueous mixture and calcining the resulting dry precursor material before or after its drying to the desired catalyst geometry at from 250 to 600° C.

20. A process as claimed in claim 1, wherein the catalyst bed comprises annular catalysts.

21. A process as claimed in claim 1, wherein the catalyst bed comprises spherical catalysts.

22. A process as claimed in claim 1, which is carried out in a two-zone tube-bundle reactor.

* * * * *